United States Patent [19]

Koide et al.

[11] 4,415,667
[45] Nov. 15, 1983

[54] CARBOXYPEPTIDASE A GAMMA AND PROCESS FOR PREPARING SAME

[75] Inventors: Atsushi Koide, Funabashi; Masayuki Yoshizawa, Kawagoe, both of Japan

[73] Assignee: Eisai Co., Ltd., Tokyo, Japan

[21] Appl. No.: 355,810

[22] Filed: Mar. 8, 1982

[30] Foreign Application Priority Data

Mar. 12, 1981 [JP] Japan ................... 56-34523

[51] Int. Cl.$^3$ .................... C12N 9/48; C12N 9/64
[52] U.S. Cl. ................... 435/212; 435/226
[58] Field of Search ............ 435/226, 219, 212

[56] References Cited

U.S. PATENT DOCUMENTS 4,071,410  1/1978  Yoshizawa .

FOREIGN PATENT DOCUMENTS 60520  9/1982  European Pat. Off. ........... 435/226

OTHER PUBLICATIONS

Eur. J. Biochem. 117, 383–388 (1981).
J. Biol. Chem. 238, 3884–3894 (1963).
Chem. Abstracts, vol. 72, No. 51151u (1970).
Chem. Abstracts, vol. 89, No. 175477a (1978).
J. Biochem. 86, 1537–1548 (1979).
Biochemistry, 4, 1750–1757 (1965).
Biochemistry, 10, 4023–4025 (1971).

Primary Examiner—Lionel M. Shapiro
Attorney, Agent, or Firm—Flynn, Thiel, Boutell & Tanis

[57] ABSTRACT

A new species of carboxypeptidase A$\gamma$ and a process for preparation thereof are disclosed. The new substance has an amino-terminal sequence with the primary structural formula of:

Asn-Tyr-Ala-Thr-Tyr-His-Thr-Leu-Glu-Glu-Ile-
Tyr-Asp-Phe-Met-Asp-Ile-Leu-Val-Ala-Glu-His-
Pro-Gln-Leu-, and has the following physiocochemical and enzymochemical properties:
  (a) state: needle crystals,
  (b) molecular weight: 38,900 (according to gel permeation method),
  (c) constituent amino acids: As listed in Table 1,
  (d) metal contained: One Zn atom per molecule,
  (e) coefficient of sedimentation: 3.3,
  (f) isoelectric point: 4.3 (at an ionic strength of 0.3),
  (g) specific substrates: N$\alpha$-carbobenzoxyglycyl-L-phenylalanine and casein,
  (h) Michaelis constant: 20 mM (N$\alpha$-carbobenzoxyglycyl-L-phenylalanine as the substrate), and
  (i) optimum pH: 7 to 8.

The new species of carboxypeptidase A$\gamma$ is extracted from porcine pancreas. The process for preparing the new species of carboxypeptidase A$\gamma$ comprises adding mammalian duodenum or an extract of mammalian duodenum to the porcine pancreas, thereby performing activation.

4 Claims, 2 Drawing Figures

CARBOXYPEPTIDASE A GAMMA AND PROCESS FOR PREPARING SAME

The present invention relates to a new species of carboxypeptidase Aγ and a process for preparing the same.

The term "carboxypeptidase" identifies a family of enzymes belonging to the peptidase group. They liberate by successive hydrolysis the terminal amino acid at the carboxyl group end of the polypeptide chain. They possess exopeptidase activity.

Carboxypeptidase A, which is one type of carboxypeptidase, is obtained from the pancreas of bovine and porcine at the present time. Carboxypeptidase A originating from these mammals liberates an amino acid from a protein substrate when the carboxyl-terminal amino acid is one other than lysine, arginine, or proline.

As for porcine pancreas carboxypeptidase A, three types of carboxypeptidase $A_1$, $A_2$, and $A_3$ are known. They were isolated by electrophoresis (Folk, J. E. & Schirmer, E. W., J. Biol. Chem. 238, 3884–3894). Afterwards, a new carboxypeptidase, called carboxypeptidase Ae, was discovered (Narayanan, A. S. & Anwar, R. A., Can. J. Biochem. 48, 7–11). Recently, a carboxypeptidase Aβ was discovered (Kobayashi, R., Kobayashi, Y., & Hirs, C. H. W., J. Biol. Chem. 253, 5526–5530).

The new species of carboxypeptidase Aγ, according to this invention, is a substance which is different from the known carboxypeptidase Aγ. It can presently be obtained only by using the new extraction method described in this specification. The new species of carboxypeptidase Aγ, of this invention, is different from known carboxypeptidase Aγ in that the primary structural formula of its amino terminal sequence and its physiocochemical and enzymochemical properties are different. The present inventors classified the new substance as a new form of carboxypeptidase Aγ, because its NH2-terminal sequence begins with Asn (asparagine). The properties which distinguish the substance of this invention are described below.

The primary structural formula of the NH2-terminal sequence of the substance of this invention is represented by:

Asn-Tyr-Ala-Thr-Tyr-His-Thr-Leu-Glu-Glu-Ile-Tyr-Asp-Phe-Met-Asp-Ile-Leu-Val-Ala-Glu-His-Pro-Gln-Leu-.

This amino-terminal sequence is not found in other forms of carboxypeptidase A. For instance, it is different from the following amino-terminal sequence of carboxypeptidase Aγ extracted from cattle pancreas:

Ala-Arg-Ser-Thr-Asn-Thr-Phe-Asn-Tyr-Ala-Thr-Tyr-His-Thr-Leu-Asp-Glu-Ile-Tyr-Asp-Phe-Met-Asp-Leu-Leu-Val-Ala-Gln-His-Pro-Glu-Leu-.

In particular, it is noted that the Glu and Ile units above in the substance of the invention are different from the corresponding units in the carboxypeptidase Aγ, Asp and Leu, as underscored above. Furthermore it is noted that the porcine carboxypeptidase Aγ of the invention has the 21st unit of Glu and the 24th of Glu while the bovine carboxypeptidase Aα has the 21st of Glu and the 24th of Glu. The bovine carboxypeptidase is disclosed in "Atlas of Protein Sequence and Structure" by M. O. Dayhoff published by National Biomedical Foundation, Washington D.C., Vol. 5(1972).

The molecular weight of the new species of carboxypeptidase Aγ of the invention, as measured by the gel permeation method, is 38,900, and each molecule contains one Zn atom. On the basis of the molecular weight 38,900, the constituent amino acids of the substance of the invention were determined to be as shown in Table 1. The total number of constituent amino acids is 347. The sedimentation coefficient $S_{20,w}$ is 3.3, which is not in great conflict with the aforesaid molecular weight 38,900 of the substance of this invention. The isoelectric point thereof is 4.3 (at an ionic strength of 0.3). Thus, when subjected to electrophoresis in a buffer solution of pH 9.4, the substance of this invention migrated toward the anode.

The substance of this invention has substrate specificity. When the carboxylic acid group at the end of the carboxyl-terminal amino acid sequence of the substrate is a free carboxylic acid, the enzyme of the invention acts as an exopeptidase, liberating the terminal amino acids by successive hydrolysis. Casein and Nα-carbobenzoxyglycyl-L-phenylalanine are specific substrates for the substance of this invention. In contrast with this, the substance of this invention does not act as an exopeptidase on substrates in which the carboxylic group of the terminal amino acid is esterified.

The substance of the present invention has one Zn atom per molecule. It loses its activity when the Zn atom is chelated by a chelating agent, such as EDTA or o-phenanthroline.

The carboxypeptidase Aγ obtained in Example 1 described below has a Michaelis constant Km of 20 mM and a maximum reaction velocity $V_{max}$ of 235.5 μmol/min/mg when the substrate is Nα-carbobenzoxyglycyl-L-phenylalanine.

The pH of optimum activity varies depending on the kind of substrate and buffer solution used. The optimum pH range is 7 to 8 when Nα-carbobenzoxyglycyl-L-phenylalanine is used as the substrate.

The external appearance of the substance of this invention is needle crystals. The form of the crystals varies slightly depending on the crystallization method used. Needle crystals are obtained in the case of crystallization from an ammonium sulfate solution.

The substance of this invention can at present be obtained only from porcine pancreas. In the process of the invention activation is performed by adding the duodenum or the extract of the duodenum of the mammal to the porcine pancreas. Activation is necessary because carboxypeptidase Aγ is normally present in a precursor form in the porcine pancreas. For the purpose of activation, the duodenum or the extract of the duodenum of the mammal is added according to this invention. Carboxypeptidase Aγ present as an inactive precursor in the porcine pancreas is thereby transformed into the active enzyme. This process was previously developed by one of the present inventors in the production of elastase. (See Japanese Patent Laid-Open No. 52-61287 [1977].) The process disclosed therein has now been successfully applied to the preparation of the new species of carboxypeptidase Aγ of this invention by the present inventors. Extraction and isolation of the enzyme after the activation step can be performed by conventional methods. Improved results can be obtained if two additional steps are included, wherein impurities are subjected to autolysis at pH 7 to 8 to facilitate their separation and the new species of carboxypeptidase Aγ is adsorbed to DEAE-Sephadex by column operation or batch operation and then is desorbed.

The autolysis of high molecular weight impurities in the extraction and isolation steps aids the subsequent separation and purification. New technology for autolysis has been discovered in the production of elastase by one of the present inventors. (See Japanese Patent Laid-Open No. 52-61287 [1977].) The technology disclosed there can also be utilized in the present invention.

Adsorption to and desorption from DEAE-Sephadex can be used as the final means for separation and purification of the new species of carboxypeptidase Aγ. Carboxypeptidase Aγ is adsorbed to DEAE-Sephadex A-50 in a buffer solution of pH 9 to 10 and is desorbed from it in a buffer solution of pH 9 to 10 containing 1 M NaCl. In a column operation, the enzyme can be adsorbed to the DEAE-Sephadex A-50 by flowing a carbonate buffer solution of pH 10.0 through the column, and can then be desorbed by flowing a carbonate buffer solution (containing 1 M NaCl) of pH 10.0 through the column. In a batch operation, the carboxypeptidase Aγ can be adsorbed to DEAE-Sephadex A-50 in, for example, a 0.05 M tris-HCl buffer solution (pH 9.4), and can then be desorbed in a 0.2 M disodium citrate solution.

DETAILED DESCRIPTION

Figure 1:
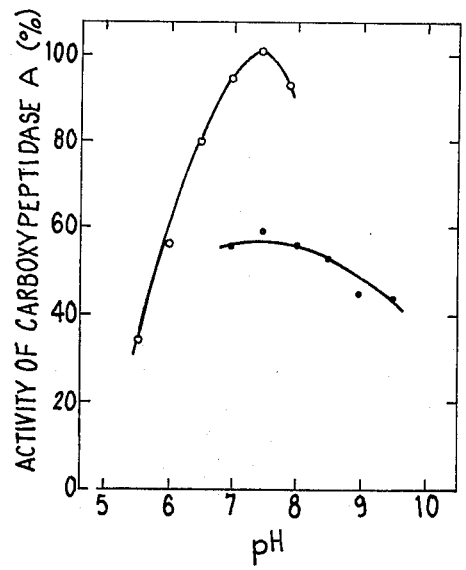
FIG. 1 is a graph in which the activity of carboxypeptidase Aγ of this invention is plotted against pH. The results obtained with a 0.01 M phosphate buffer solution (containing 0.1 M NaCl) are indicated by small circles; the results obtained with a 0.02 M Veronal buffer solution (containing 0.1 M NaCl) are indicated by dots. The activity of carboxypeptidase Aγ is its hydrolase activity on a Nα-carbobenzoxyglycyl-L-phenylalanine substrate.
Figure 2:
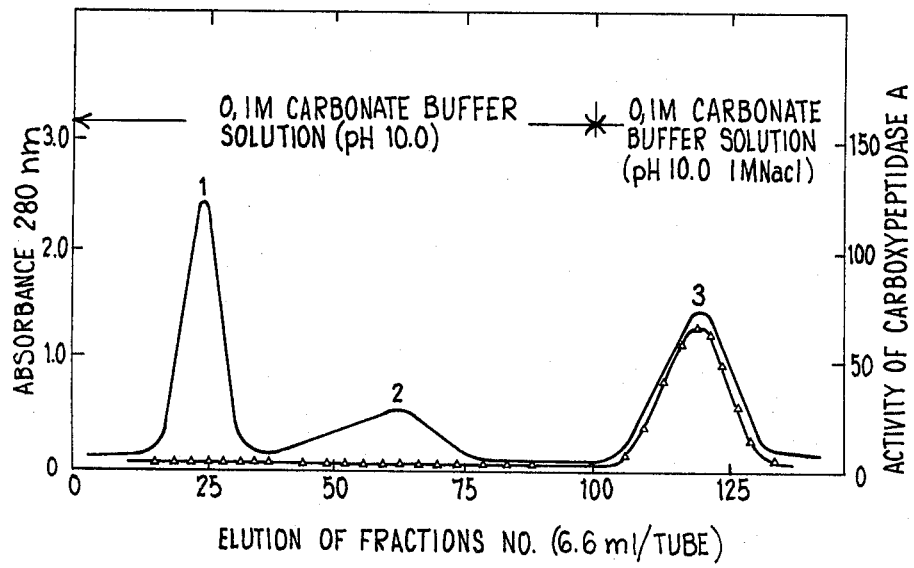
FIG. 2 is a graph showing the elution curves. The solid line represents the quantities of protein (determined by absorbance at 280 nm) plotted against the fractions sequentially obtained from the column. The line with triangle symbols represents the activity of carboxypeptidase A plotted against the fractions. For the elution of the fractions up to No. 100, a 0.1 M carbonate buffer solution (pH 10.0) was used as the eluting agent. For elution of fractions of No. 100 and above, a 0.1 M carbonate buffer solution (pH 10.0, containing 1 M NaCl) was used as the eluting agent. The activity of carboxypeptidase Aγ is its hydrolase activity on a Nα-carbobenzoxyglycyl-L-phenylalanine substrate, that is, the quantity (μmol/min/ml) of phenylalanine liberated by hydrolysis.

Experiments were carried out on the sample of carboxypeptidase Aγ obtained in Example 1 described below in order to study the structure and properties of the substance of the invention.

EXPERIMENTS (1) Primary structural formula of amino-terminal sequence

The primary structural formula of the amino-terminal sequence was determined using Beckmann Sequencer Model 890, according to Edman & Begg's method modified by Hermodson et al. The sample was carboxymethylated by reduction, and then the decomposed amino acid (PTH amino acid: phenylthiohydantoic amino acid) was identified by high pressure liquid chromatography. The primary structural formula of the NH2-terminal sequence containing 25 terminal amino acid residues was identified as follows:

Asn-Tyr-Ala-Thr-Tyr-His-Thr-Leu-Glu-Glu-Ile-
Tyr-Asp-Phe-Met-Asp-Ile-Leu-Val-Ala-Glu-His-
Pro-Gln-Leu-.

The three-letter symbols stand for the following amino acid residues.
Asn: Asparagine
Gln: Glutamine
Leu: Leucine
Tyr: Tyrosine
His: Histidine
Met: Methionine
Pro: Proline
Asp: Aspartic acid
Glu: Glutamic acid
Ile: Isoleucine
Thr: Threonine
Phe: Phenylalanine
Val: Valine
Ala: Alanine (2) Molecular weight The molecular weight of the carboxypeptidase Aγ was obtained by the Sephadex G-200 gel permeation technique, according to the Andrews method. According to this method, a 0.1 M phosphate buffer solution (pH 8.3, containing 1 M NaCl) was flowed through the column at a velocity of 20 ml/hour, and the absorbance at 280 nm was determined for the eluate fractions. As proteins of known molecular weight, soybean trypsin inhibitor (molecular weight 21,500), elastase (molecular weight 25,000), ovalbumin (molecular weight 45,000), cattle serum albumin (molecular weight 67,000), and γ-globulin (molecular weight 160,000) were used. The molecular weight was determined by comparing the eluate volumes. It was found that the molecular weight of the new species of carboxypeptidase Aγ was 38,900.

(3) Constituent amino acids

The constituent amino acids of the enzyme of the invention were determined by using a Durrum Model D-500 amino acid analyzer. Table 1 shows the constituent amino acids on the basis of a molecular weight 38,900.

TABLE 1

| Amino acid | Number |
|---|---|
| Lysine | 15 |
| Histidine | 10 |
| Arginine | 12 |
| Aspartic acid and asparagine | 36 |
| Threonine | 27 |
| Serine | 28 |
| Glutamic acid and glutamine | 32 |
| Proline | 16 |
| Glycine | 28 |
| Alanine | 24 |
| Cystine | 2 |
| Valine | 15 |
| Methionine | 4 |
| Isoleucine | 27 |
| Leucine | 25 |
| Tyrosine | 18 |
| Phenylalanine | 19 |
| Tryptophan | 9 |
| Total | 347 |

(4) Metal contained

After wet washing, a sample of the invention enzyme was measured for atomic absorption at 2140 Å using a Hitachi Model 303 atomic absorption spectrophotometer. It was found that each molecule contained one Zn atom.

(5) Sedimentation coefficient

The sedimentation coefficient of the sample enzyme was determined using a Spinco Model E ultracentrifuge for a sample dissolved at a concentration of 1.0 mg/ml in a 0.1 M phosphate buffer solution (pH 7.0). It was found that the sedimentation coefficient $S_{20,w}$ was 3.3.

(6) Isoelectric point

The isoelectric point was determined by paper electrophoresis according to the Kunkel & Tiselius method, in which Whatman No. 1 filter paper was used. The sample was dissolved in an acetate buffer solution ($\mu=0.3$) and subjected to electrophoresis for 5 hours under 120 volts at room temperature. As the control substance, D-xylose was used. It was found that the isoelectric point was 4.3.

(7) Activation optimum pH

The activation optimum pH was determined using, as the substrate, 20 mM N$\alpha$-carbobenzoxyglycyl-L-phenylalanine in a 0.05 M NaCl solution. The buffer solutions used were a 0.01 M phosphate buffer solution (containing 0.1 M NaCl) and a 0.02 M Veronal buffer solution (containing 0.1 M NaCl). The results are shown in FIG. 1.

(8) Substrate specificity

The enzyme activity of the enzyme of the invention for N$\alpha$-carbobenzoxyglycyl-L-phenylalanine substrate was investigated by the ninhydrin method. That is, 0.1 ml of a 0.02 M substrate solution was added to a 0.01 M phosphate buffer solution (pH 7.5, containing 0.1 M NaCl). After the combined solutions stood at 25° C. for 5 minutes, 0.2 ml of an enzyme solution was added, and the solution was incubated at 25° C. for 15 minutes. The reaction was stopped by adding 1 ml of a 3 M acetate buffer solution (pH 5.0) in an ice bath. The ninhydrin reagent was added to effect color development according to the Yemn & Cocking method. The enzyme activity for a casein substrate was investigated by the Kunitz method. Enzyme activities of the enzyme of the invention for benzoylglycyl-L-arginine and elastin were also investigated by the respective methods above. Enzyme activity was observed only for N$\alpha$-carbobenzoxyglycyl-L-phenylalanine and casein.

(9) Michaelis constant and maximum reaction velocity

The reaction velocity was obtained for samples wherein the concentrations of the substrate N$\alpha$-carbobenzoxylglycyl-L-phenylalanine were varied from 0.02 to 0.1 M. It was found that the Michaelis constant Km was 20 mM and the maximum reaction velocity $V_{max}$ was 235.5 $\mu$mol/min/mg.

(10) Inhibition of activity

A sample of the enzyme according to the invention was dissolved at a concentration of 130 $\mu$g/ml in a 0.01 M phosphate buffer solution (pH 7.5). 5 ml of this solution was dialyzed into 1000 ml of a 0.01 M phosphate buffer solution (pH 7.5) containing 1 mM of EDTA or o-phenanthroline. A portion of the dialyzate was diluted with a 0.01 M phosphate buffer solution (pH 7.5, containing 0.2 M NaCl), and the residual activity was then determined for N$\alpha$-carbobenzoxyglycyl-L-phenylalanine. It was found that the activity was inhibited by 34% when EDTA was employed and by 87% when o-phenanthroline was employed.

The enzyme substance of this invention can be stored in a 0.005 M phosphate buffer solution (pH 5.8, ammonium sulfate saturation 17%) containing a few drops of toluene in a cool place. The substance of the invention is expected to exhibit great utility in aiding protein digestion in the digestive tract. In addition, it can be used to determine the primary structure (sequence) of proteins and peptides.

The invention is illustrated by the following example.

EXAMPLE 1

A fresh swine pancreas was minced and mixed with 3 liters of a 0.1 M sodium acetate solution at a temperature in the range of 15° to 20° C. To this mixture was added 100 g of minced porcine duodenum. The pH was adjusted to 7.3 with 2 N NaOH, and stirring was continued for 16 hours at 10° C.

The pH was then adjusted to 5.3 with 2 N acetic acid. Insolubles were removed by centrifugation, with Celite 545 being added in an amount of 200 g per liter. Ammonium sulfate was added to the resulting supernatant liquid until the degree of saturation reached 45%. The resulting liquid was allowed to stand overnight at 3° C.

The resulting precipitates (183 g) were collected by filtration, and then dissolved in 1.1 liters of a 0.1 M potassium phosphate solution (pH 7.0). A dark brown solution was obtained. This solution was allowed to stand for 20 hours at 20° C. On filtration through a filter paper, a clear solution was obtained.

Ammonium sulfate was added to this solution until the degree of saturation reached 35%. After pH adjustment to 6.5, this solution was allowed to stand overnight in a cool place. The resulting precipitates were collected by filtration, and dissolved in 0.21 liter of a 0.1 M sodium carbonate solution (pH 7.0). The pH was readjusted to exactly 7.0, and stirring was continued for 3 days at 5° C.

Fine needle crystals separated out of the solution. They were collected by centrifugation, followed by washing by suspension in cold water and filtration.

The resulting crystals were crude carboxypeptidase A$\gamma$. These crystals were purified as follows by a batch operation with DEAE-Sephadex A-50.

The crude carboxypeptidase A$\gamma$ crystals were suspended in a 0.05 M tris-HCl buffer solution (pH 9.4). The pH was adjusted to 11.0 with 2 N NaOH so as to dissolve the crystals completely. The pH was then readjusted to 9.4. 75 g of DEAE-Sephadex A-50 which had previously been equilibrated with a 0.05 M tris-HCl buffer solution were added to this solution. The mixture was stirred slowly for 4 hours at 5° C. The Sephadex gel was collected by filtration and washed with 3 liters of a 0.05 M tris-Hcl buffer solution (pH 9.4) and 0.5 liter of water. The resulting wet Sephadex cake was transformed into a slurry by adding 90 ml of a 0.2 M sodium citrate solution, followed by stirring for 2 hours. The carboxypeptidase A$\gamma$ was thereby desorbed from the DEAE-Sephadex A-50. After filtration, ammonium sulfate was added to the filtrate so that the degree of saturation was 70%. The pH was adjusted to 5.5, and the solution was allowed to stand overnight in a cool place.

The resulting precipitates were collected and dissolved in a small quantity of water. Insolubles were removed by centrifugation, and the clear liquid was dialyzed into water. The resulting precipitates collected by centrifugation were dissolved in a 0.005 M sodium phosphate solution (pH 5.8, ammonium sulfate saturation 17%). Insolubles were removed by centrifugation, and the pH was adjusted to 5.8. The liquid was allowed to stand for one week at 5° C. The crystals which separated out were collected by centrifugation. Crystals of the new species of carboxypeptidase Aγ were thereby obtained.

We claim:

1. A carboxypeptidase Aγ substance in which the NH$_2$-terminal sequence containing 25 amino acid residues is as follows:

Asn-Tyr-Ala-Thr-Tyr-His-Thr-Leu-Glu-Glu-Ile-Tyr-Asp-Phe-Met-Asp-Ile-Leu-Val-Ala-Glu-His-Pro-Gln-Leu-, said substance having the following properties:
(a) physical state = needle crystals
(b) molecular weight, according to gel permeation method = 38,900
(c) constituent amino acids =

TABLE 1

| Amino acid | Number |
|---|---|
| Lysine | 15 |
| Histidine | 10 |
| Arginine | 12 |
| Aspartic acid and asparagine | 36 |
| Threonine | 27 |
| Serine | 28 |
| Glutamic acid and glutamine | 32 |
| Proline | 16 |
| Glycine | 28 |
| Alanine | 24 |
| Cystine | 2 |
| Valine | 15 |
| Methionine | 4 |

TABLE 1-continued

| Amino acid | Number |
|---|---|
| Isoleucine | 27 |
| Leucine | 25 |
| Tyrosine | 18 |
| Phenylalanine | 19 |
| Tryptophan | 9 |
| Total | 347 |

(d) metal contained = one Zn atom per molecule
(e) coefficient of sedimentation $S_{20,w} = 3.3$
(f) isoelectric point, at an ionic strength of 0.3 = 4.3
(g) specific substrates = Nα-carbobenzoxyglycyl-L-phenylalanine and casein
(h) Michaelis constant (Nα-carbobenzoxyglycyl-L-phenylalanine as the substrate) = 20 mM
(i) pH of optimum activity = 7 to 8.

2. A carboxypeptidase Aγ substance as claimed in claim 1, which has been extracted from porcine pancreas.

3. A process for preparing a carboxypeptidase Aγ substance as claimed in claim 1, which comprises extracting an inactive precursor of said substance from porcine pancreas, then mixing said precursor with mammalian duodenum or extract thereof under conditions effective to activate said substance; and then recovering said substance.

4. A process as claimed in claim 3 in which said substance is recovered by contacting a buffer solution having a pH of from 9 to 10 which is free of NaCl and which contains said substance, with DEAE-Sephadex so that said substance is adsorbed to said DEAE-Sephadex and then contacting said DEAE-Sephadex with a buffer solution having a pH of 9 to 10 and containing 1 M NaCl to thereby desorb said substance from said DEAE-Sephadex.

* * * * *